United States Patent
Paul et al.

(10) Patent No.: US 8,118,809 B2
(45) Date of Patent: *Feb. 21, 2012

(54) FLEXIBLE CONDUCTIVE POLYMER ELECTRODE AND METHOD FOR ABLATION

(75) Inventors: Saurav Paul, Minnetonka, MN (US); Hong Cao, Savage, MN (US); Chou Thao, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1083 days.

This patent is subject to a terminal disclaimer.

(21) Appl. No.: 11/963,430

(22) Filed: Dec. 21, 2007

(65) Prior Publication Data

US 2009/0163916 A1    Jun. 25, 2009

(51) Int. Cl.
*A61B 18/14* (2006.01)

(52) U.S. Cl. .......................................... 606/41

(58) Field of Classification Search .............. 606/32–50; 607/101–105
See application file for complete search history.

(56) References Cited

U.S. PATENT DOCUMENTS

| | | | |
|---|---|---|---|
| 4,945,912 A | 8/1990 | Langberg | |
| 5,122,137 A | 6/1992 | Lennox | |
| 5,246,438 A | 9/1993 | Langberg | |
| 5,334,193 A | 8/1994 | Nardella et al. | |
| 5,433,708 A | 7/1995 | Nichols | |
| 5,542,928 A | 8/1996 | Evans | |
| 5,755,760 A | 5/1998 | Maguire et al. | |
| 5,788,692 A * | 8/1998 | Campbell et al. | 606/33 |
| 6,053,912 A | 4/2000 | Panescu et al. | |
| 6,280,441 B1 | 8/2001 | Ryan | |
| 6,312,425 B1 | 11/2001 | Simpson et al. | |
| 6,477,396 B1 * | 11/2002 | Mest et al. | 600/374 |
| 6,514,250 B1 | 2/2003 | Jahns et al. | |
| 6,522,930 B1 | 2/2003 | Schaer et al. | |
| 6,939,350 B2 * | 9/2005 | Phan | 606/49 |
| 6,986,769 B2 | 1/2006 | Nelson et al. | |
| 7,163,537 B2 * | 1/2007 | Lee et al. | 606/41 |
| 7,311,704 B2 | 12/2007 | Paul | |
| 7,326,204 B2 | 2/2008 | Paul et al. | |
| 7,326,205 B2 | 2/2008 | Paul et al. | |
| 7,326,206 B2 | 2/2008 | Paul et al. | |
| 2003/0004506 A1 * | 1/2003 | Messing | 606/41 |
| 2003/0060822 A1 * | 3/2003 | Schaer et al. | 606/41 |
| 2003/0088244 A1 * | 5/2003 | Swanson et al. | 606/41 |
| 2006/0161151 A1 * | 7/2006 | Privitera et al. | 606/41 |
| 2006/0178666 A1 * | 8/2006 | Cosman et al. | 606/41 |
| 2006/0217701 A1 | 9/2006 | Young et al. | |
| 2006/0287650 A1 * | 12/2006 | Cao et al. | 606/41 |

(Continued)

*Primary Examiner* — Linda Dvorak
*Assistant Examiner* — Daniel Fowler
(74) *Attorney, Agent, or Firm* — Wiley Rein LLP

(57) ABSTRACT

An electrode for ablation therapy includes a flexible conductive element for conducting electrical energy and a flexible conductive polymer member in electrically conductive contact with the conductive element. A catheter shaft may be coupled to the conductive element and/or the flexible conductive polymer member. The flexible conductive element may be formed as a helical coil, a mesh coating or wrap, or any other suitable form, and may surround (wholly or partially) a flexible electrically insulative, and optionally thermally conductive, member. A heat sink may be thermally coupled to at least one of the flexible conductive polymer member and the flexible electrically insulative member. The flexible electrically insulative member may include a passageway for coolant fluid to cool the electrode during ablation. The passageway may include at least one efflux hole to permit coolant fluid to flow from the passageway, or may define a closed loop.

49 Claims, 15 Drawing Sheets

U.S. PATENT DOCUMENTS

| | | |
|---|---|---|
| 2007/0005053 A1* | 1/2007 | Dando .............................. 606/41 |
| 2007/0027448 A1* | 2/2007 | Paul et al. ........................ 606/41 |
| 2007/0066972 A1* | 3/2007 | Ormsby et al. .................. 606/41 |
| 2007/0083195 A1* | 4/2007 | Werneth et al. ................. 606/41 |
| 2007/0112342 A1* | 5/2007 | Pearson et al. .................. 606/34 |
| 2007/0270791 A1* | 11/2007 | Wang et al. ..................... 606/41 |
| 2008/0161889 A1* | 7/2008 | Paul et al. ...................... 607/102 |

* cited by examiner

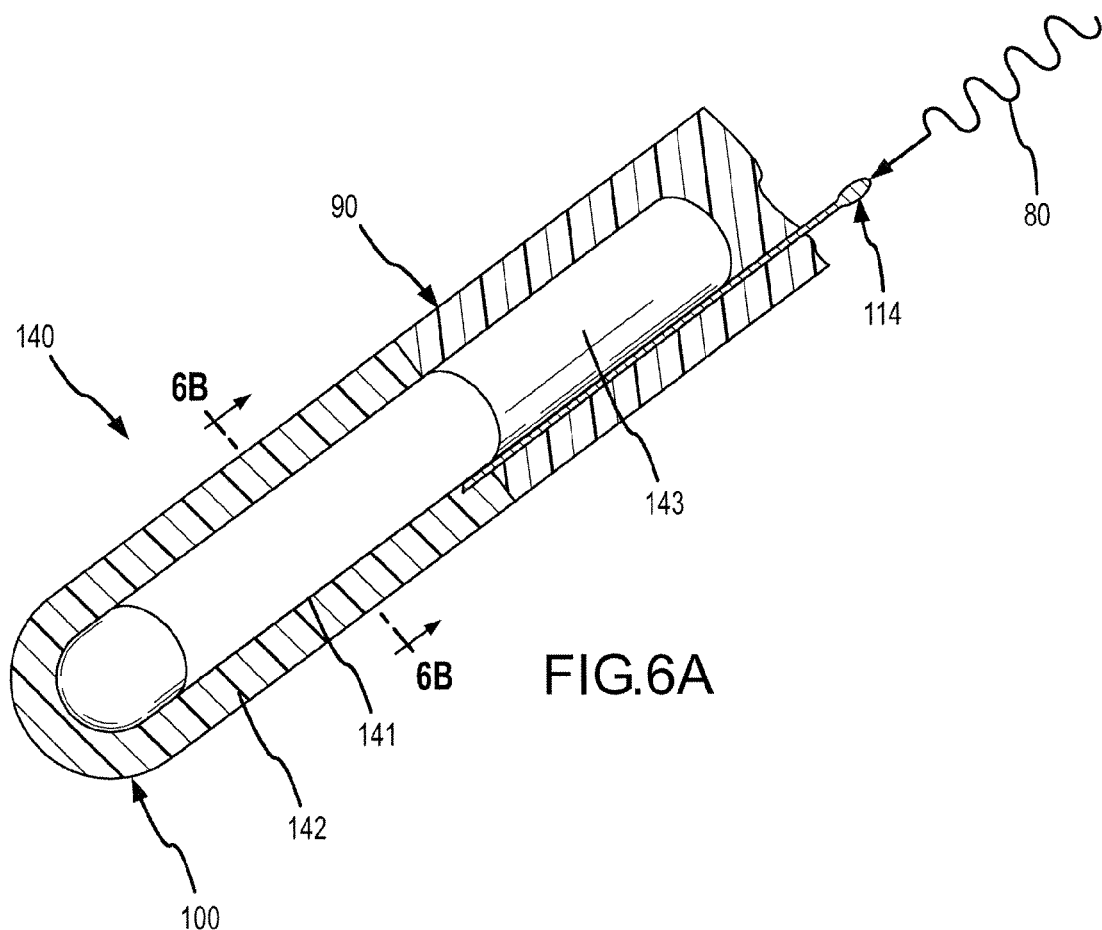
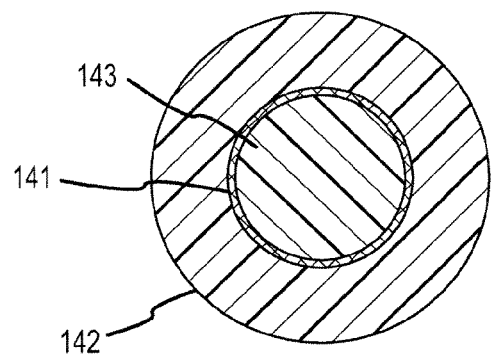
FIG.6A
FIG.6B

FLEXIBLE CONDUCTIVE POLYMER ELECTRODE AND METHOD FOR ABLATION

CROSS-REFERENCE TO RELATED APPLICATIONS

This application is related to U.S. application Ser. No. 11/963,321, filed 21 Dec. 2007, which is hereby incorporated by reference in its entirety as though fully set forth herein.

BACKGROUND OF THE INVENTION a. Field of the Invention

The present invention pertains generally to an electrophysiological device and method for providing energy to biological tissue and, more particularly, to an ablation apparatus with improved device-to-tissue contact.

b. Background Art

Ablation devices, including radiofrequency ("RF") ablation devices, have heretofore been provided, but not using conductive polymer electrodes.

Many medical procedures, including for example, creating lesions with electrical energy, rely on good contact between the medical device and the tissue. In some catheter applications, the point of electrode-tissue contact is typically 150 cm away from the point of application of force. This gives rise to functional and theoretical challenges associated with conventional devices, and thus, the ability to accurately assess tissue contact is increasingly important, especially in connection with ablation treatment.

There is a need for improved ablation devices that provide greater contact sensitivity for control of ablation treatments using electrical energy.

There is a need for improved ablation devices that provide greater contact sensitivity for RF ablation treatments.

There is also a need for improved ablation devices that better concentrate the RF energy to the region of tissue that is in contact with the electrode.

BRIEF SUMMARY OF THE INVENTION

The present invention provides for ablation devices and methods having improved contact properties utilizing flexible conductive polymers.

An objective of the present invention is to provide a flexible conductive polymer electrode that may be used for RF ablation treatment.

Another object of the present invention is to provide a method of manufacturing an electrode assembly for ablation therapy.

Another object of the present invention is to provide a flexible, conductive polymer-based electrode for RF ablation, which can be used in a wide variety of tissue environments.

Yet another object of the invention is to provide an ablation electrode that better concentrates the energy to the region of tissue that is in contact with the electrode.

Yet another object of the invention is to provide an ablation electrode that mitigates edge-effects, hot spots and coagulum formation during the ablation process.

A further object of the invention is to provide a system for RF ablation treatment, including an RF generator and a coolant supply system that can be connected to a flexible, conductive polymer-based electrode to provide control over the RF ablation process.

Another object of the present invention is to provide an electrode with a contact sensor assembly that can sense contact with tissue based on the pressure that is exerted on the sensor, and then use the contact information for medical treatments (such as ablation).

Another object of the present invention is to provide an ablation electrode with a contact sensor that measures pressure that is being exerted on the sensor based on direct or indirect contact between the sensor and another mass, such as tissue.

Yet another object of the present invention is to provide a method of ablation using contact sensing.

Yet another objective of this invention is to provide a method for RF ablation that utilizes a flexible, conductive polymer-based electrode in accordance with the teachings herein.

Still another object of the invention is to provide an irrigated, flexible conductive polymer electrode.

Disclosed herein is an electrode for ablation therapy. The electrode includes a flexible conductive element for conducting electrical energy and a flexible conductive polymer member that is in electrically conductive contact with the conductive element. Optionally, the electrode includes a catheter shaft coupled to at least one of the conductive element and the flexible conductive polymer member. It may also include an ablation energy source coupled to the conductive element such that ablation energy may be delivered via the flexible conductive polymer member.

The flexible conductive element may be formed as a helical coil, a mesh coating or wrap, or any other suitable form. The flexible conductive element may surround, partially or wholly, a flexible electrically insulative, and optionally thermally conductive, member. It is also contemplated that at least one temperature sensor may be located within the flexible electrically insulative member.

To further enhance cooling of the electrode, a heat sink may be thermally coupled to at least one of the flexible conductive polymer member and the flexible electrically insulative member. Alternatively, or in addition, the flexible electrically insulative member may include a passageway for coolant fluid to cool the electrode during ablation. The passageway may include at least one efflux hole (e.g., an efflux hole at a distal end of the electrode, a plurality of efflux holes arranged along a length of the electrode, or one or more efflux holes positioned at an interface between the electrode and the catheter shaft) to permit coolant fluid to flow from the passageway ("open irrigation"). Alternatively, the passageway may define a loop such that coolant fluid travels from a proximal end of the electrode, through a distal end of the electrode, and returns to the proximal end of the electrode via the passageway ("closed-loop irrigation"). Typically, the coolant fluid passageway is defined by a flexible, electrically insulative, and thermally conductive material, and may be defined at least in part by the flexible electrically conductive member about which the flexible conductive element is formed.

In some embodiments of the invention, temperature sensors are provided, for example to measure the temperature of the coolant fluid. Thus, a first sensor may measure the temperature of the coolant fluid near the efflux hole and a second sensor may measure the temperature of the coolant fluid at a location other than the efflux hole, such as where the coolant fluid enters the passageway. Of course, it is contemplated that the temperature sensors may measure other temperatures (e.g., electrode temperatures, tissue temperatures, blood temperatures, and the like).

In another embodiment of the invention, an ablation electrode for ablation therapy includes: a flexible electrically insulative member, the member also being thermally conductive; a passageway for a coolant fluid to flow through the flexible electrically insulative member to cool the electrode during use; a flexible, conductive element for conducting RF energy, the flexible conductive element at least partially covering the flexible electrically insulative member; and a layer of flexible conductive polymer that covers at least part of the flexible conductive element.

The passageway may include at least one efflux hole in the electrode to permit coolant fluid to flow from the passageway. Alternatively, the passageway may define a loop such that coolant fluid travels from a proximal end of the electrode, through a distal end of the electrode, and returns to the proximal end of the electrode via the passageway.

In some embodiments of the invention, the passageway is defined by an electrically and thermally insulative material that is different from that comprising the electrically insulative member, and the electrode also includes: a first sensor to measure the temperature of coolant fluid where it exits one of the at least one efflux hole; and a second sensor to measure the temperature of coolant fluid where it enters the passageway.

In still another aspect of the invention, a method of manufacturing an electrode for ablation therapy generally includes the steps of: forming an electrically insulative, thermally conductive, flexible shaft; forming a flexible, electrically conductive element for conducting RF energy, the conductive element at least partially covering the electrically insulative, thermally conductive, flexible shaft; and forming a layer of flexible conductive polymer that covers at least part of the flexible, electrically conductive element. The step of forming an electrically insulative, thermally conductive, flexible shaft may include forming an electrically insulative, thermally conductive, flexible shaft, having a passageway through which coolant fluid may flow and having an efflux hole at a distal end of the electrode to permit coolant fluid to flow from the passageway.

The method may also include forming an electrically insulative, thermally conductive passageway within the electrically insulative, thermally conductive, flexible shaft, the passageway being formed of a material that is different from the material that is used to form the electrically insulative, thermally conductive, flexible shaft.

Also disclosed is a method of treating tissue, generally including the following steps: providing an electrode having a) a flexible conductive element for conducting RF energy and b) a layer of flexible conductive polymer that is in electrical contact with at least a portion of the flexible conductive element; coupling an RF energy supply to the flexible conductive element; positioning the electrode in contact with a tissue specimen to be treated; and delivering RF energy to the tissue specimen. Optionally, a coolant fluid may be delivered to an area of the tissue specimen to help control the temperature of the tissue specimen during treatment with RF energy. Further, it is contemplated that temperatures may be monitored at a plurality of locations within the electrode in order to help control the temperature of the tissue specimen during treatment with RF energy. A heat sink thermally coupled to the electrode may be used to help control the temperature of the tissue specimen during treatment with RF energy.

In another embodiment, the invention provides an electrode for ablation therapy, including: a conductive element for conducting electrical energy; a flexible conductive polymer member in electrically conductive contact with the conductive element; and at least one fluid passageway extending through at least a portion of the flexible conductive polymer member and including at least one efflux hole to permit a fluid to exit the flexible conductive polymer member. The at least one efflux hole may be a single efflux hole located at a distal end of the electrode, a plurality of efflux holes arranged along a length of the electrode, or any other arrangement. The at least one fluid passageway may be defined by at least one electrically insulative, and optionally also thermally conductive, tube.

The electrode may also include a catheter shaft coupled to at least one of the conductive element and the flexible conductive polymer member. The catheter shaft will typically include at least one fluid passageway that is in fluid communication with the at least one fluid passageway of the electrode. Thus, it is also contemplated that the at least one efflux hole may be located at an interface between the ablation electrode and the catheter shaft.

In still another aspect of the present invention, a method of manufacturing a tissue ablation device includes the steps of: forming a conductive element; forming an ablation electrode by covering at least a portion of the conductive element with a flexible conductive polymer material; and forming at least one fluid passageway in the ablation electrode, the at least one fluid passageway including at least one efflux hole to permit a fluid to exit the ablation electrode. The step of forming at least one fluid passageway in the ablation electrode may include providing at least one electrically insulative tube extending through at least a portion of the flexible conductive polymer material, and the step of forming a conductive element may include forming a conductive element covering at least part of the at least one electrically insulative tube. Of course, the method may also include providing a catheter shaft having a distal end and at least one fluid passageway extending at least partway therethrough and coupling the ablation electrode to the distal end of the catheter shaft such that the at least one fluid passageway of the catheter shaft is in fluid communication with the at least one fluid passageway of the ablation electrode.

In yet a further aspect of the invention, a method of treating tissue is disclosed. The method generally includes: providing an electrode including a flexible conductive element for conducting ablation energy, a flexible conductive polymer material covering at least a portion of the conductive element, and a fluid passageway including at least one efflux hole that permits a fluid to exit the electrode; coupling an ablation energy supply to the conductive element; positioning the electrode in contact with a tissue specimen to be treated; delivering ablation energy to the tissue specimen; and flowing a coolant through the fluid passageway to cool the electrode.

An advantage of using a flexible conductive polymer in an ablation device is that the design may be significantly less complicated, which permits reduced manufacturing costs and increased reliability.

Another advantage of using a flexible conductive polymer electrode in an ablation device is improved contact between the electrode and the tissue, which results in a higher efficiency in delivering ablation energy to the tissue.

Another advantage of using an irrigated flexible conductive polymer electrode is that the flexibility of the electrode permits greater effective contact, thereby improving tissue cooling (e.g., conductive tissue cooling).

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 6A and 6B are cross-sectional views of another preferred embodiment in which the electrode is in the shape of a mesh.

DETAILED DESCRIPTION OF THE INVENTION

Figure 1A:
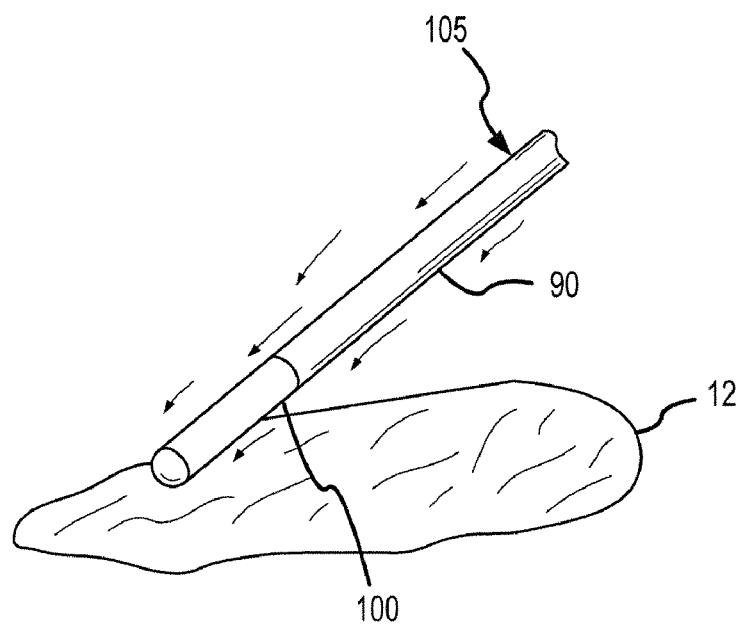
FIGS. 1A and 1B are perspective views of a sample embodiment of the present invention, illustrating how the present invention may be used to ablate tissue.

A flexible conductive polymer electrode for ablation is disclosed, along with methods for using and methods of manufacturing the flexible conductive polymer electrode. Of course, it is within the spirit and scope of the present invention to use the flexible conductive polymer electrode for other applications, including, but not limited to, electrophysiology studies such as mapping and diagnosis.

As used herein, the term "conductive polymer" refers to a polymer that is formed using at least some conductive materials and which is conductive even in its quiescent state such that the polymer may conduct sufficient energy to ablate tissue. The present invention will work with various conductive polymer materials. For example, U.S. Pat. No. 6,999,821, which is hereby incorporated by reference as though fully set forth herein, discloses intrinsically conductive and conductor-filled polymers that may be useful in the present invention. As disclosed therein, intrinsically conductive polymers include polyacetylene, polypyrrole, and polyanaline, among others. Conductor-filled polymers may include presently available materials approved for implantation such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637.

The substrate need not be silicone; for example, it is contemplated that other insulating or weakly conductive materials (e.g., non-conductive elastomers) may be embedded with conductive materials, conductive alloys, and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium, and metals of the lanthanide and actinide series, and, if appropriate, at least one electroconductive agent). The conductive material may be in the form of powder, grains, fibers, or other shaped forms. The oxides can be mixtures comprising sintered powders of an oxycompound. The alloy may be conventional, for example titanium boride.

Other examples of conductive polymers that may be used in the present invention include the conductive polymers described and disclosed in U.S. Pat. Nos. 6,646,540, 6,495,069, and 6,291,568, all of which are incorporated by reference as if set forth in their entireties herein.

The conductive polymer may be pressure sensitive, in that the electrical resistance of the electrode may vary inversely in proportion to the pressure that is applied thereto. It should be understood, however, that the flexible conductive polymer electrodes disclosed herein are conductive even in their quiescent state (that is, when not under stress), and are therefore distinguished from the pressure sensitive conductive composite ("PSCC") electrodes disclosed in U.S. application Ser. No. 11/647,316, filed 29 Dec. 2007, which are non-conductive in their quiescent state. Preferably, the conductive polymer material will also meet cytotoxity, hemolysis, systemic toxicity and intracutaneous injection standards.

Figure 1B:
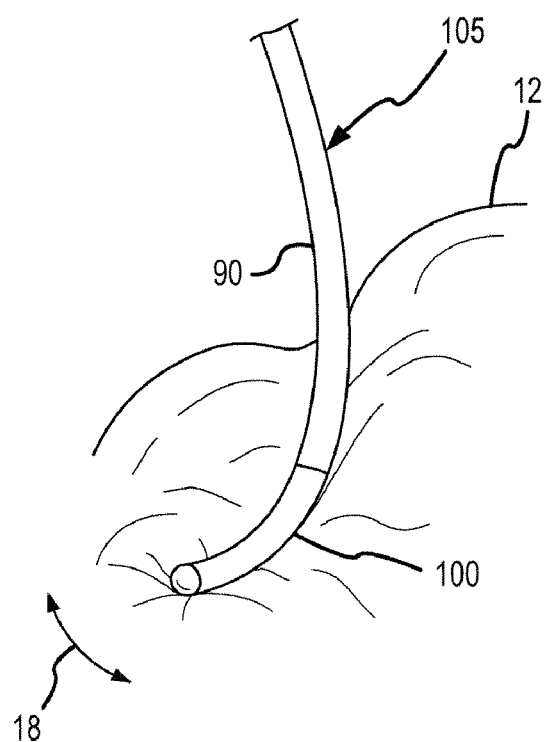

FIGS. 1A and 1B illustrate a sample embodiment of the present invention. As illustrated in FIGS. 1A and 1B, a flexible conductive polymer electrode 105 generally includes a catheter shaft 90 and a contact surface 100 that extends from catheter shaft 90. Electrode 105 is flexible such that when it comes into contact with tissue 12, electrode 105 is deflected in direction 18 as illustrated in FIG. 1B, thereby increasing the contact surface between electrode 105 and tissue 12. Advantageously, this increased contact surface improves the efficacy of, for example, the delivery of ablating energy to the tissue. One of skill in the art will recognize that increasing the force on electrode 105 will tend to increase the contact between electrode 105 and tissue 12, as tissue 12 will tend to "wrap around" electrode 105.

Figure 2:
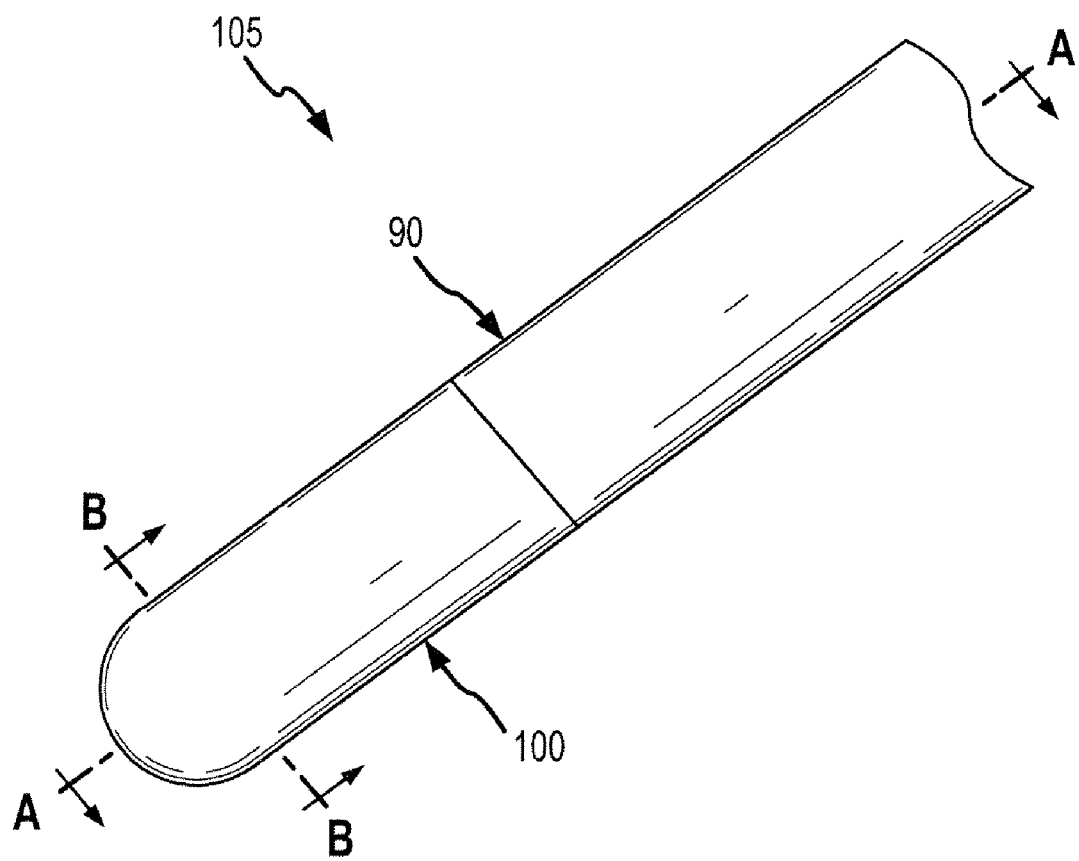
FIG. 2 is a side view drawing of an exemplary catheter having a flexible conductive polymer electrode.

FIG. 2 is a close-up of the sample embodiment depicted in FIGS. 1A and 1B. FIG. 2 illustrates cross-sectional reference lines A-A and B-B, which will be used to illustrate preferred embodiments of the present invention.

Figure 3A:
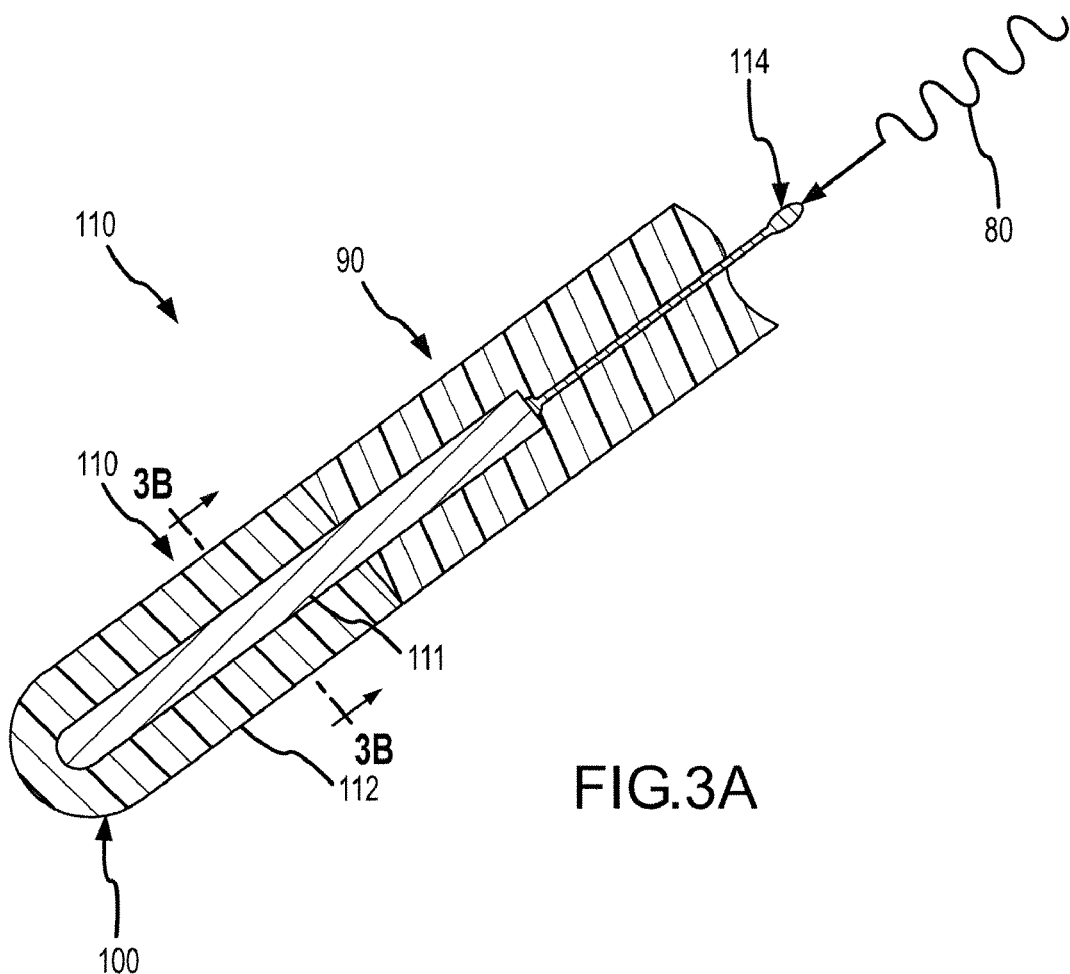
FIGS. 3A and 3B are cross-sectional views of a preferred embodiment of a catheter having a flexible conductive polymer electrode.
Figure 3B:
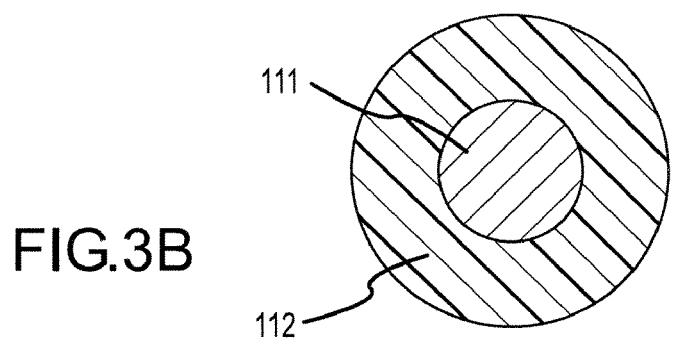

FIGS. 3A and 3B illustrate a preferred embodiment of the present invention, revealing two cross sectional drawings taken along the reference lines of A-A and B-B as labeled in FIG. 2. In this preferred embodiment, the electrode 110 includes catheter shaft 90 and a contact surface 100 that extends from catheter shaft 90. Catheter shaft 90 may be either conductive or non-conductive, and preferably, catheter shaft 90 is non-conductive. In this embodiment, the flexible conductive polymer forms the working surface of the electrode that is used for ablation therapy. As depicted in FIGS. 3A and 3B, electrode 110 includes a flexible inner conductive core 111 and an outer conductive polymer substrate layer 112, which is mechanically and electrically coupled to the flexible inner conductive core 111. Flexible inner conductive core 111 may include a flat top (like the top of a right cylinder), or optionally it may include a portion of a sphere on its distal end as illustrated in FIG. 3A. Flexible inner conductive core 111 may be connected to an electrical conductor 114, which may be connected to an RF generator (e.g., RF current source 80). In use, this preferred embodiment is used to ablate tissue (not shown) to which a reference electrode (not shown) has been attached. Electrode 110 ablates tissue by delivering ablation energy through inner conductive core 111. Preferably, the reference electrode is grounded to an electrical ground.

Figure 4A:
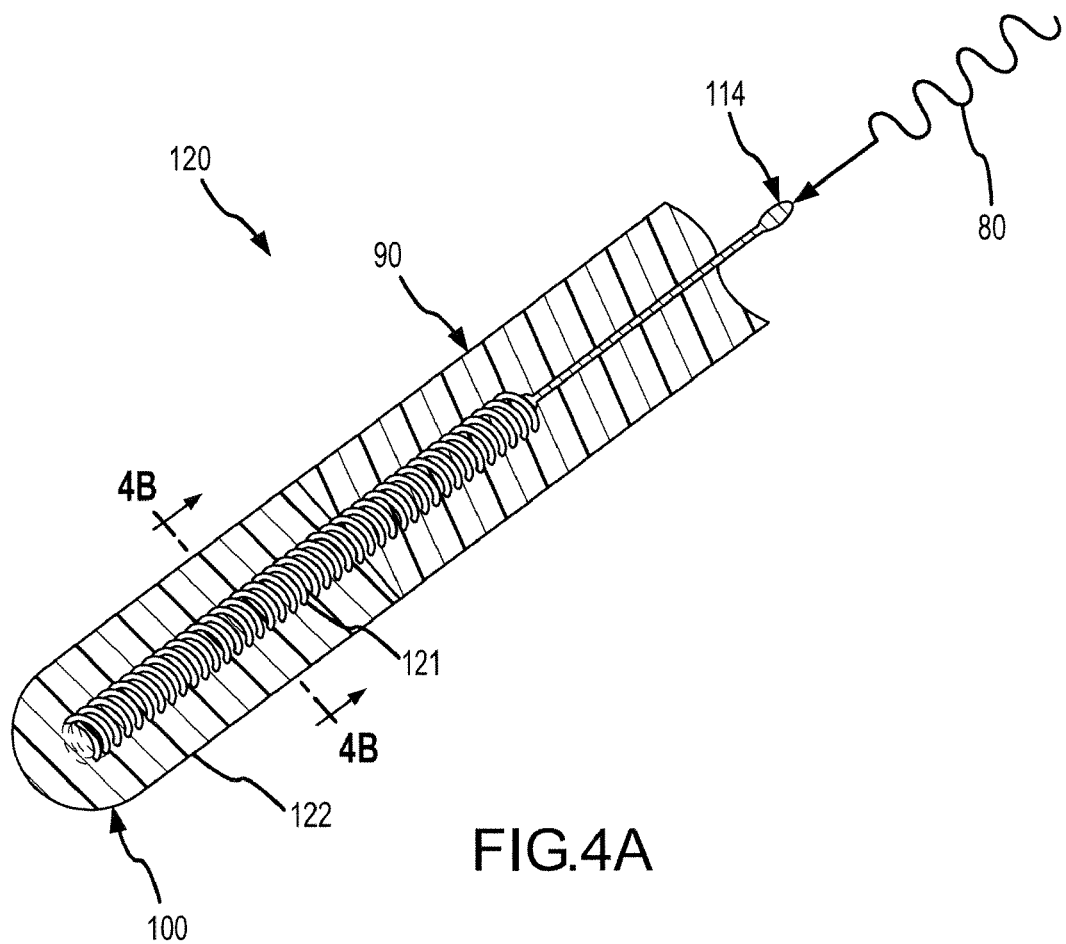
FIGS. 4A and 4B are cross-sectional views of another preferred embodiment in which the electrode is in the shape of a helix.
Figure 4B:
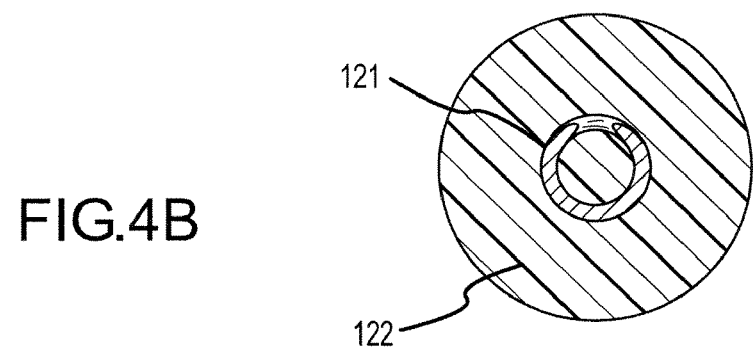

FIGS. 4A and 4B illustrate another preferred embodiment of the present invention, revealing two cross sectional drawings taken along the reference lines of A-A and B-B as labeled in FIG. 2. Electrode 120 extends from a catheter shaft 90 and generally includes flexible inner conductive coil 121 in the shape of a helix and a flexible conductive polymer substrate layer 122 within which the inner conductive coil 121 is located. Flexible inner conductive coil 121 is connected to an electrical conductor 114, which may be connected to an RF generator (e.g., RF current source 80). In use, this preferred embodiment is used to ablate tissue (not shown) to which a reference electrode (not shown) has been attached. Electrode 120 ablates tissue by delivering ablation energy through inner conductive coil 121. Preferably, the reference electrode is grounded to an electrical ground.

Figure 5A:
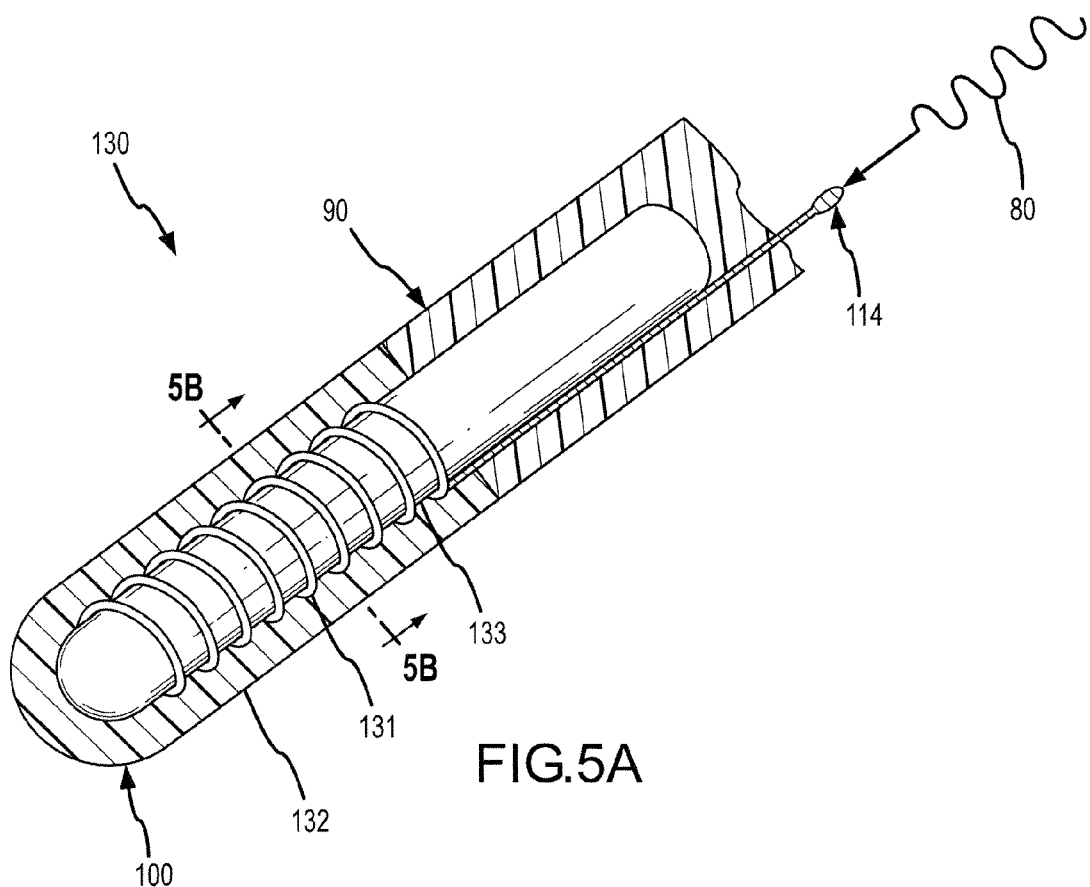
FIGS. 5A and 5B are cross-sectional views of another preferred embodiment in which the electrode is located about a flexible inner core.
Figure 5B:
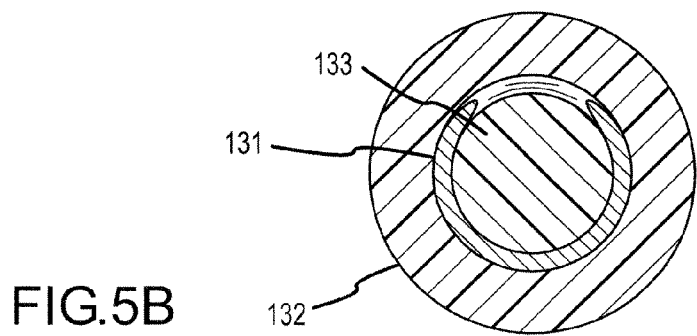

FIGS. 5A and 5B illustrate yet another preferred embodiment of the present invention, revealing two cross sectional drawings taken along the reference lines of A-A and B-B as labeled in FIG. 2. Electrode 130 extends from a catheter shaft 90 and generally includes: flexible inner conductive coil 131 in the shape of a helix; an outer flexible conductive polymer substrate layer 132; and a flexible shaft 133 located within the helix of the flexible inner conductive coil 131.

Flexible shaft 133 is preferably an electrically insulative shaft, but may be electrically conductive without departing from the spirit and scope of the present invention. Moreover, flexible shaft 133 is preferably thermally conductive, as described in further detail below. Flexible shaft 133 may optionally include a portion of a sphere on its distal end as shown in FIG. 5A.

Flexible inner conductive coil 131 is connected to an electrical conductor 114, which may be connected to an RF generator (e.g., RF current source 80). In use, this preferred embodiment is used to ablate tissue (not shown) to which a reference electrode (not shown) has been attached. Electrode 130 ablates tissue by delivering energy through inner conductive coil 131. Preferably, the reference electrode is grounded to an electrical ground reference signal.

FIGS. 6A and 6B illustrate yet another preferred embodiment of the present invention, revealing two cross sectional drawings taken along the reference lines of A-A and B-B as labeled in FIG. 2. Electrode 140 extends from a catheter shaft 90 and generally includes: flexible inner conductive sheath 141 formed of a mesh; an outer flexible conductive polymer substrate layer 142; and a flexible shaft 143, which is preferably electrically insulative, located interiorly of the flexible inner conductive sheath 141. Flexible shaft 143 may optionally include a portion of a sphere at its distal end as shown in FIG. 6A. Flexible sheath 141 is connected to an electrical conductor 114, which may be connected to an RF generator (e.g., RF current source 80). In use, this preferred embodiment is used to ablate tissue to which a reference electrode (not shown) has been attached. Electrode 140 ablates tissue by delivering energy through the flexible sheath 141. Preferably, the reference electrode is grounded to an electrical ground reference signal.

Figure 7A:
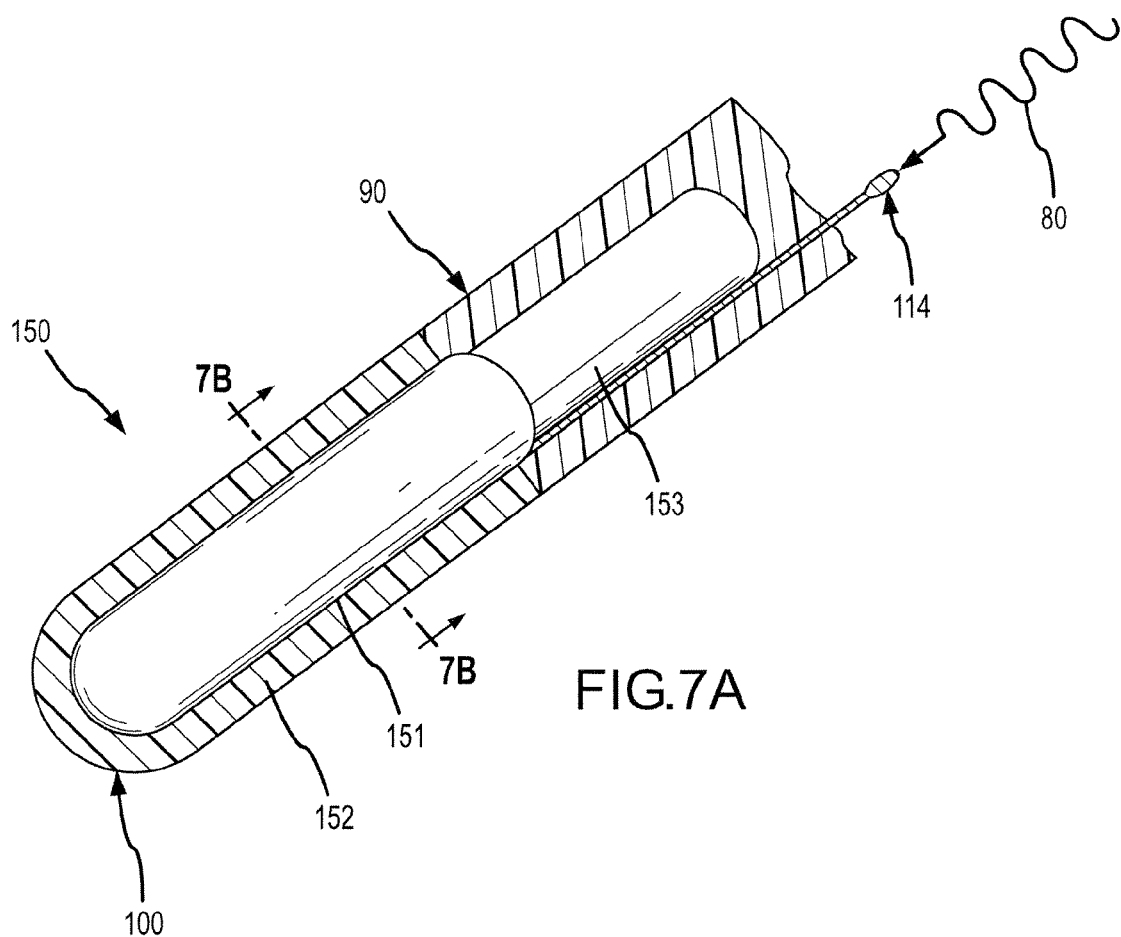
FIGS. 7A and 7B are cross-sectional views of another preferred embodiment in which the flexible conductive polymer electrode is formed as an outer substrate layer.
Figure 7B:
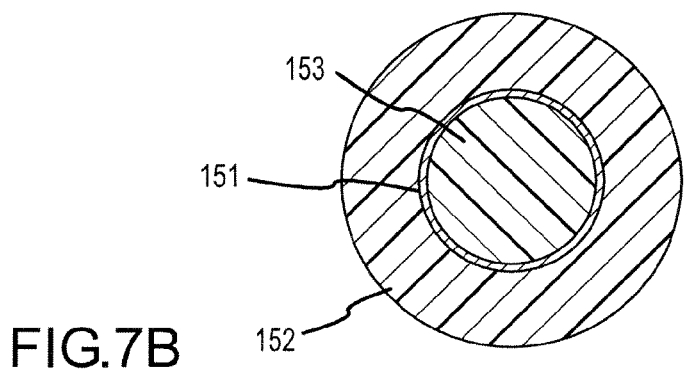

FIGS. 7A and 7B illustrate yet another preferred embodiment of the present invention, revealing two cross sectional drawings taken along the reference lines of A-A and B-B as labeled in FIG. 2. Electrode 150 extends from a catheter shaft 90 and generally includes: an electrically insulative flexible shaft 153; a flexible inner conductive layer 151 (formed, for example, as a coating and/or wrap around flexible shaft 153); and an outer flexible conductive polymer substrate layer 152. Electrically insulative flexible shaft 153 and flexible inner conductive layer 151 may optionally include a portion of a sphere at their respective distal ends (as illustrated in FIG. 7A). Flexible inner conductive core 151 is connected to an electrical conductor 114, which may be connected to an RF generator (e.g., RF current source 80). In use, this preferred embodiment is used to ablate tissue (not shown) to which a reference electrode (not shown) has been attached. Electrode 150 ablates tissue by delivering ablation energy through the flexible inner conductive core 151. Preferably, the reference electrode is grounded to an electrical ground reference signal.

Figure 8A:
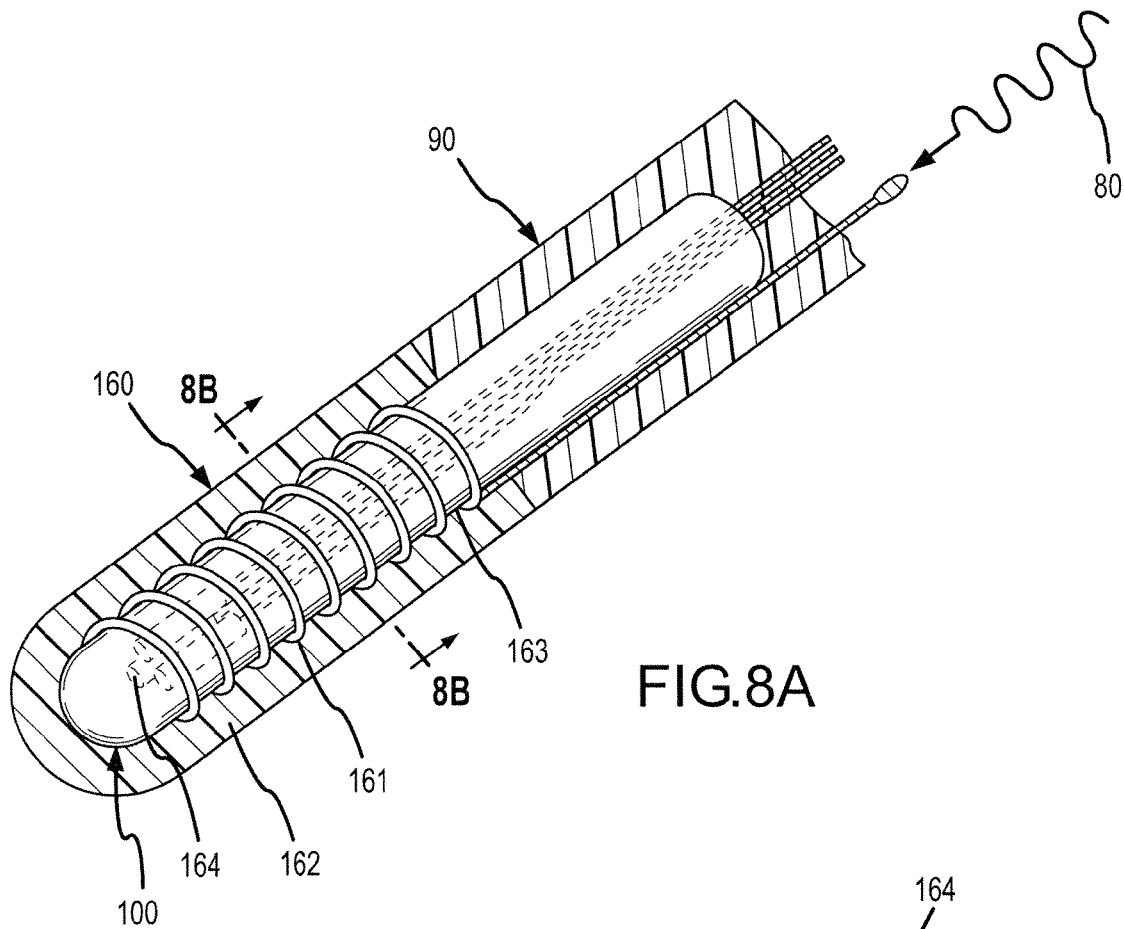
FIGS. 8A and 8B are cross-sectional views of yet another preferred embodiment of the invention with thermal sensing.
Figure 8B:
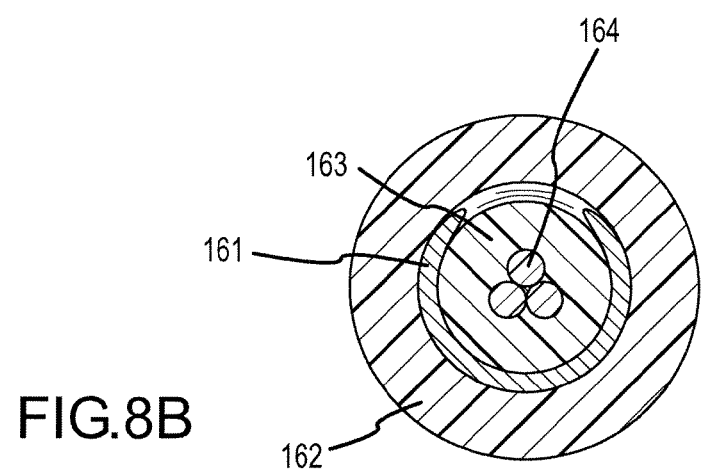

FIGS. 8A and 8B illustrate yet another preferred embodiment of the present invention, revealing two cross sectional drawings taken along the reference lines of A-A and B-B as labeled in FIG. 2. Electrode 160 extends from a catheter shaft 90 and generally includes a thermally conductive, electrically insulative, flexible shaft 163; a flexible inner conductive layer 161 (formed, for example, as a coating and/or wrap around flexible shaft 163, or as illustrated in FIG. 8, a helix); an outer flexible conductive polymer substrate layer 162; and a plurality of thermal sensors 164 located within the thermally conductive, electrically insulative, flexible shaft 163 to measure temperatures at various locations therein. Electrically insulative flexible shaft 163 and flexible inner conductive layer 161 may optionally include a portion of a sphere at their respective distal ends (as illustrated in FIG. 8A). Flexible inner conductive coil 161 is connected to an electrical conductor 114, which may be connected to an RF generator (e.g., RF current source 80). In use, this preferred embodiment is used to ablate tissue (not shown) to which a reference electrode (not shown) has been attached. Electrode 160 ablates tissue by delivering ablation energy through the flexible inner conductive coil 161. Preferably, the reference electrode is grounded to an electrical ground reference signal.

As one of ordinary skill can appreciate, temperature sensors 164 (such as thermistors, thermocouples or other temperature sensors) can be used to monitor operation temperature to help ensure effective and safe ablation treatment. For example, one or more temperatures may be used at a variety of locations, including, for example, at a distal end of the device to monitor a temperature that is at least in part reflective of the tissue temperature, or even within the electrically insulative shaft. Other potential locations include the use of a temperature sensor located at a location where a cooling fluid enters or exits the device. Of course, temperature sensors may be located at additional or different locations.

Figure 9A:
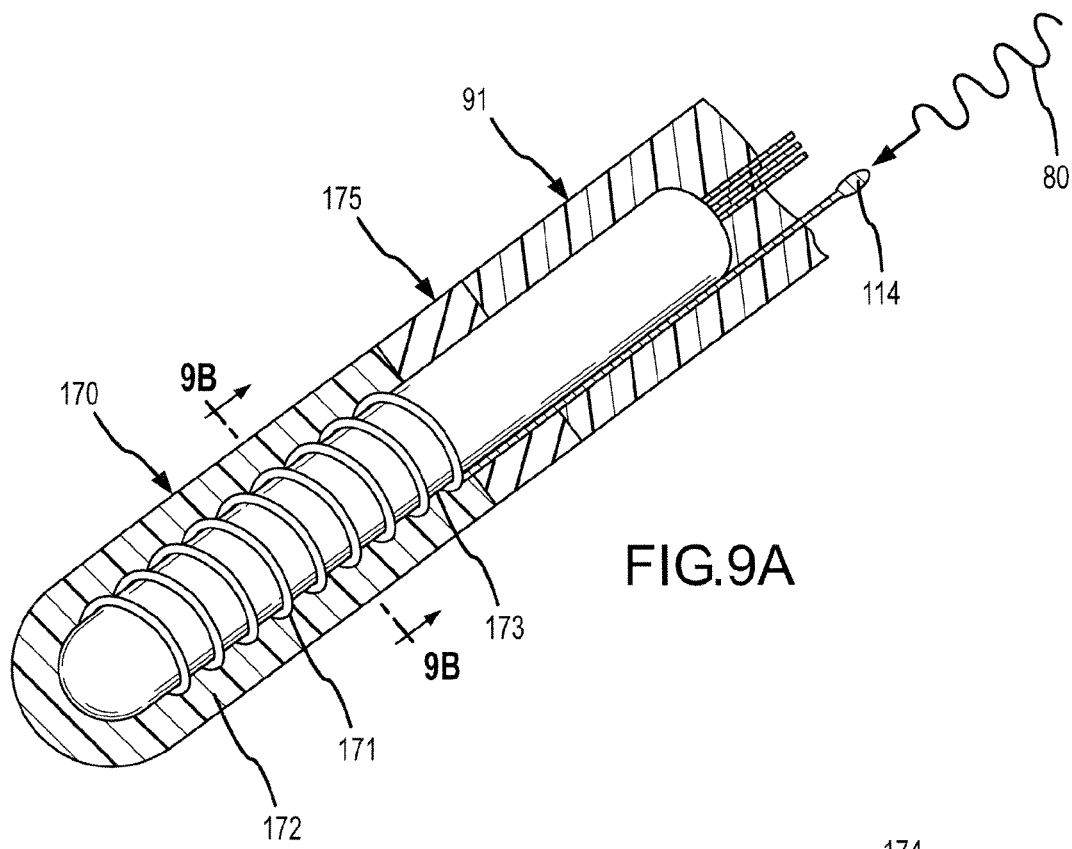
FIGS. 9A and 9B are cross-sectional views of another preferred embodiment in which the electrode is adjacent a heat sink.
Figure 9B:
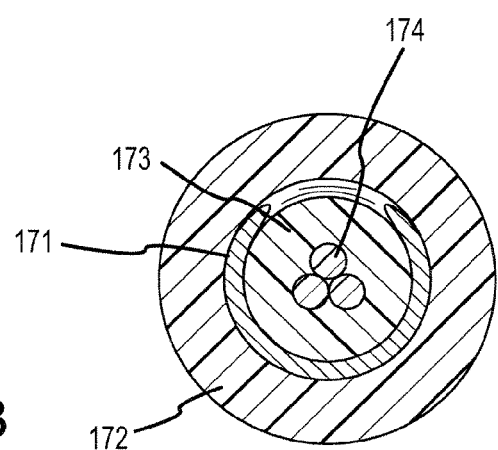

FIGS. 9A and 9B illustrate yet another preferred embodiment of the present invention, revealing two cross sectional drawings taken along the reference lines of A-A and B-B as labeled in FIG. 2. Electrode 170 extends from a catheter shaft 90 and generally includes: a thermally conductive, electrically insulative, flexible shaft 173; a flexible inner conductive layer 171 (formed, for example, as a coating and/or wrap around flexible shaft 173, or as illustrated in FIG. 9, a helix); an outer flexible conductive polymer substrate layer 172; a heat sink 175 thermally coupled to flexible shaft 173; and a plurality of thermal sensors 174 located within the thermally conductive, electrically insulative, flexible shaft 173 to measure temperatures at various locations therein. Electrically insulative flexible shaft 173 and flexible inner conductive layer 171 may optionally include a portion of a sphere at their respective distal ends (as illustrated in FIG. 9A). Flexible inner conductive coil 171 is connected to an electrical conductor 114, which may be connected to an RF generator (e.g., RF current source 80). In use, this preferred embodiment is used to ablate tissue (not shown) to which a reference electrode (not shown) has been attached. Electrode 170 ablates tissue by delivering ablation energy through the flexible inner conductive coil 171. Preferably, the reference electrode is grounded to an electrical ground reference signal.

As one of ordinary skill can appreciate, temperature sensors 174 (such as thermistors, thermocouples or other temperature sensors) can be used to monitor operation temperature to help ensure effective and safe ablation treatment. Heat sink 175 helps to prevent the electrode from overheating the electrode and the tissue.

Electrical conductor 114 may be implemented using a single conductive wire or multiple strands of wire. Preferably, the wires are made of flexible conductive materials which allow the surface contacting area of the electrode to be bent and formed into various shapes to provide better contact with the tissue (e.g., an increased contact area between the electrode and the tissue). Acceptable materials include, but are not limited to, stainless steel, nickel titanium (e.g., Nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

The present invention permits the construction of a flexible conductive polymer RF ablation electrode that can be used in a wide variety of different tissue environments, including for example, tissues having varying degrees of elasticity and contour.

While the preferred embodiments disclosed in the attached figures disclose an electrode that is generally cylindrical in shape, the present invention also contemplates that the electrode may be formed into various shapes to better fit the contour of the target tissue. In one embodiment, for example, the electrode can be made long enough to strap around and form a noose around the pulmonary veins in epicardial applications. Particularly, electrical conductor 114 that is coupled to the RF energy source may be formed into a desired shape and then the flexible conductive polymer layer may be formed over the conductive element in the preferred shape. For example, the electrode may be shaped like a spatula for certain applications, including for example, minimally invasive sub-xyphoid epicardial applications, where the spatula shape will permit easy placement and navigation in the pericardial sac. Because the conductive polymers used herein are flexible materials, they can be used to form electrodes having a great variety of shapes, including a spatula.

Alternatively, the electrically conductive element that is coupled to the RF energy source (for example, 111, 121, 131, 141, 151, 161 and 171) may be formed using shape-memory retaining material, such as Nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133, 143, 153, 163, and 173) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the RF energy source be formed in the shape of a helix, such as is the case with elements 121, 131, 161 and 171, the coil may be chosen to be of a specific stiffness (that is, having a characteristic spring constant) that would allow the coil to exert a desired amount of pressure when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 4, 5 and 6, the conductive element may be mounted on an insulative shaft. The conductive element can be shaped in any number of ways, including for example, a coil, mesh, coating or wrap. The insulative shaft provides additional mechanical support in applications that require greater amounts of axial force and torque. The insulative shaft may be made of any electrically insulative material, including, for example, polyurethane. Preferably, the insulative shaft is made of a biocompatible, electrically insulative material.

Generally, flexibility is a very desirable characteristic in a catheter. Some applications, however, may require relatively more or less flexibility. Thus, it is contemplated that the same structural design may be used to produce ablation devices of varying flexibility, for example by varying the materials employed in constructing the ablation device.

In other embodiments, for example, as depicted in FIGS. 7A and 8A, the conductive element is mounted on an electrically insulative, thermally conductive shaft. The thermally conductive shaft may improve the cooling of the electrode and the electrode-tissue interface temperature during ablation by thermally conducting the heat from the interface to the ambient flowing blood in endocardial applications. In addition, the thermally conductive shaft can be instrumented with thermal sensors (for example, as depicted in FIGS. 7 and 8) that can be used for temperature controlled RF ablation. The thermally conductive shaft may be made of any electrically insulative, thermally conductive material, including, for example, CoolPoly® thermally conductive, electrically insulative plastic. Preferably, the thermally conductive shaft is made of a biocompatible, thermally conductive, electrically insulative material.

In yet another embodiment, for example, as depicted in FIG. 9A, the cooling efficiency of the ablation electrode can be enhanced by mounting a heat sink 175 at the proximal end of the active electrode 170. The heat sink comprises a material with high thermal conductivity. The use of a heat sink may be particularly useful for small electrodes (typically around 10 mm or less), or for sectioned electrodes that may give rise to hot spots. The heat sink may be made of any electrically insulative, thermally conductive material, including, for example, thermally conductive polyurethane (e.g., polyurethane with thermally conductive ceramic powder embedded therein), diamond, aluminum nitride, boron nitride, silicone, thermal epoxy and thermally conductive, electrically insulative plastics. Preferably, the thermally conductive shaft is made of a biocompatible, thermally conductive, electrically insulative material.

In yet another embodiment, the electrically insulative member may contain one or more passageways for carrying cooling fluids (e.g., saline solution) to the distal end of the electrode. Alternatively, one or more of the passageways may be further defined by a cooling tube made of the same material as, or a material different from, the insulative member. Of course, it is contemplated that the cooling tube and the electrically insulative member may be one in the same (that is, the electrically insulative member itself may define the fluid passageway). If a cooling tube is used in addition to the passageway, the portion of the cooling tube that is located within the catheter shaft is preferably thermally and electrically insulative, while the portion of the cooling tube that is located within the electrode is preferably thermally conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

In yet another embodiment, the electrically insulative member may contain one or more passageways for carrying cooling fluids to the actual electrode-tissue interface. The passageways include an inlet to the electrode, and at least one outlet, such as a fluid efflux hole at the distal end of the electrode. Moreover, one or more thermal sensors may be placed in or near the fluid passageway, for example, to measure the temperature of the coolant at the inlet and/or at the outlet. The temperature difference between the inlet and outlet during ablation could be used to monitor the efficacy of the electrode-tissue interface cooling and also to perform temperature-controlled ablation. One or more of the passageways may alternatively be further defined by a cooling tube, which may be made of the same material as, or a material different from, the insulative member, and which, in some embodiments, may be at least partially defined by the insulative member. If a cooling tube is used in addition to the passageway, the portion of the cooling tube that is located within the catheter shaft is preferably thermally insulative, while the portion of the cooling tube that is located within the electrode is preferably thermally and electrically conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

Figure 10:
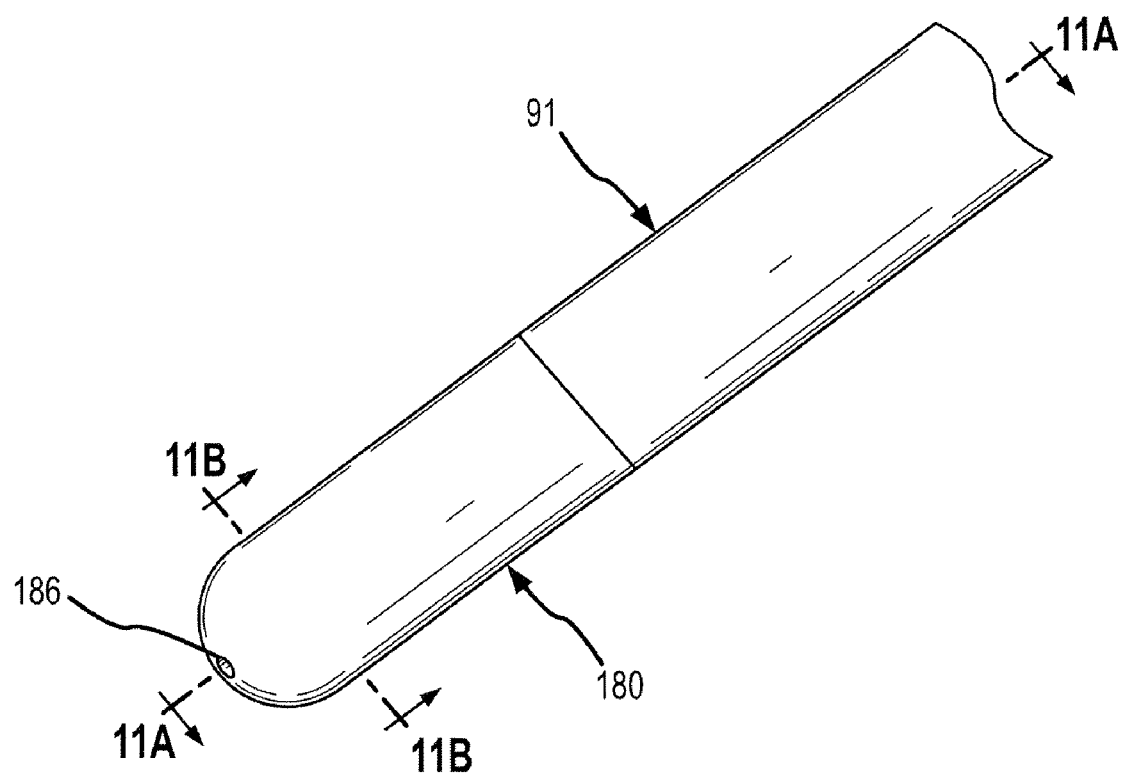
FIG. 10 is a side view of another preferred embodiment of the invention in which the catheter includes a coolant efflux hole.

FIG. 10 illustrates a specific preferred embodiment for the invention of the present application. Electrode 180 extends from a catheter shaft 91 and is connected to an RF energy source (not shown). Electrode 180 further comprises coolant efflux hole 186 that permits the coolant flowing through the core of the catheter from stagnating (and thus heating) inside the catheter. The efflux hole helps to ensure that a fresh supply of coolant is available to keep the working portion of the catheter cool. One of ordinary skill will appreciate that efflux hole 186 could be utilized with any of the preceding embodiments.

It is contemplated that one or more fluid efflux holes may be provided to permit the coolant to exit the electrode. For example, electrode 180 may include a single coolant efflux hole 186 at its distal end as illustrated in FIG. 10. Alternatively, multiple fluid efflux holes may be arranged along electrode 180, for example along its length and/or around its circumference. It may also be desirable to include one or more fluid efflux holes at the junction between electrode 180 and catheter shaft 91.

An irrigated electrode as described above advantageously enhances cooling of both the electrode and the tissue being treated. The coolant flowing through the fluid passageways and out the efflux holes cools the electrode first, and then cools the adjacent tissue by thermal conduction. The flexibility of the irrigated electrode permits the electrode to more closely conform to the tissue surface. This conformance increases the contact area between the electrode and the tissue being treated, which in turn enhances conductive heat transfer from and cooling of the tissue.

Figure 11A:
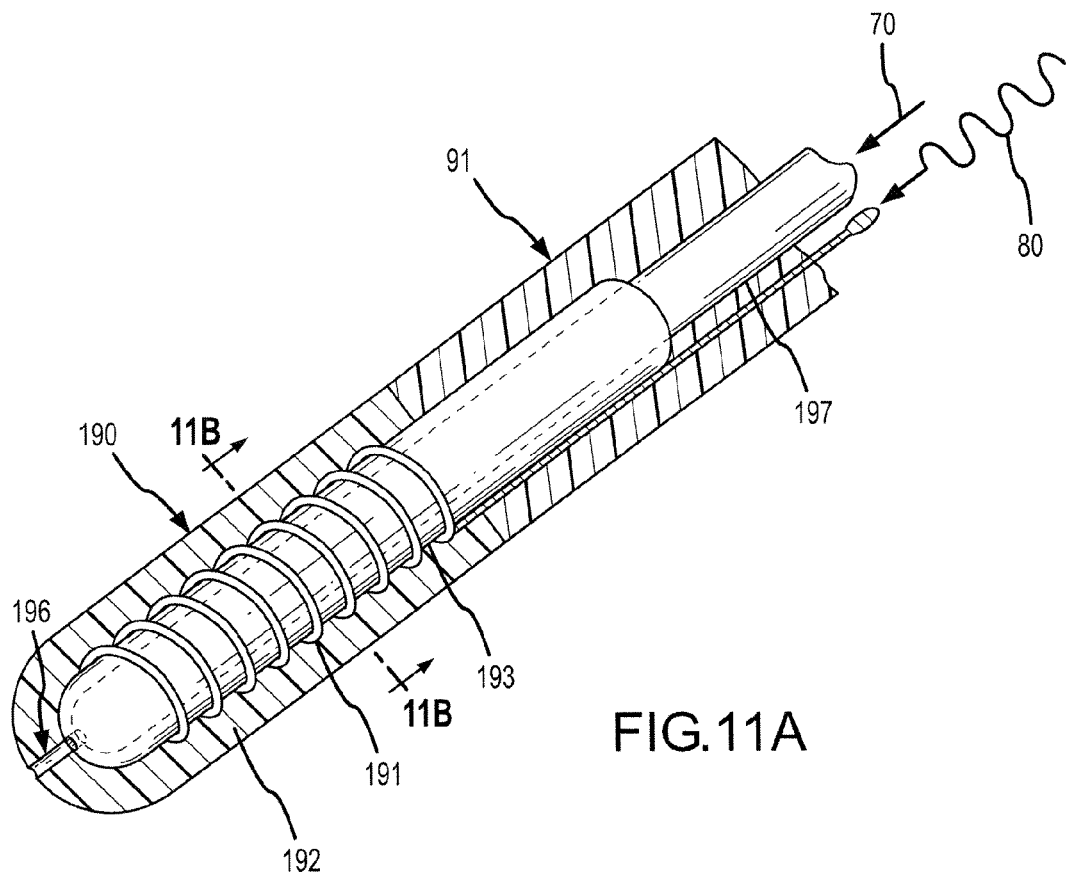
FIGS. 11A and 11B are cross-sectional views of a modified version of the embodiment of FIGS. 5A and 5B including a fluid efflux hole.
Figure 11B:
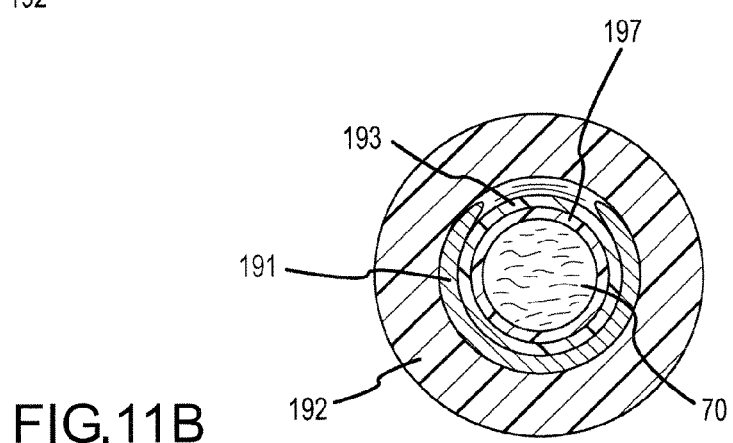

FIGS. 11A and 11B illustrate another preferred embodiment. More particularly, FIGS. 11A and 11B illustrate a modification to the embodiment of FIG. 5 in which efflux hole 196 has been added. Electrode 190 extends from a catheter shaft 91 and is connected to an RF energy source (e.g., RF current source 80). Electrode 190 generally includes: flexible inner conductive coil 191 in the shape of a helix; an outer flexible conductive polymer substrate layer 192; a thermally conductive, electrically insulative flexible tube 193 located partially within the helix of the flexible inner conductive coil 191; and a coolant efflux hole 196. Note that a thermally insulative tube 197 is used in at least a portion of the catheter shaft 91 to help reduce the likelihood of cooling fluid 70 (e.g., saline solution) being heated to body temperature. In this embodiment, note that thermally conductive, electrically insulative flexible tube 193 also forms the thermally conductive, electrically insulative, flexible shaft which is present in other embodiments.

Figure 12A:
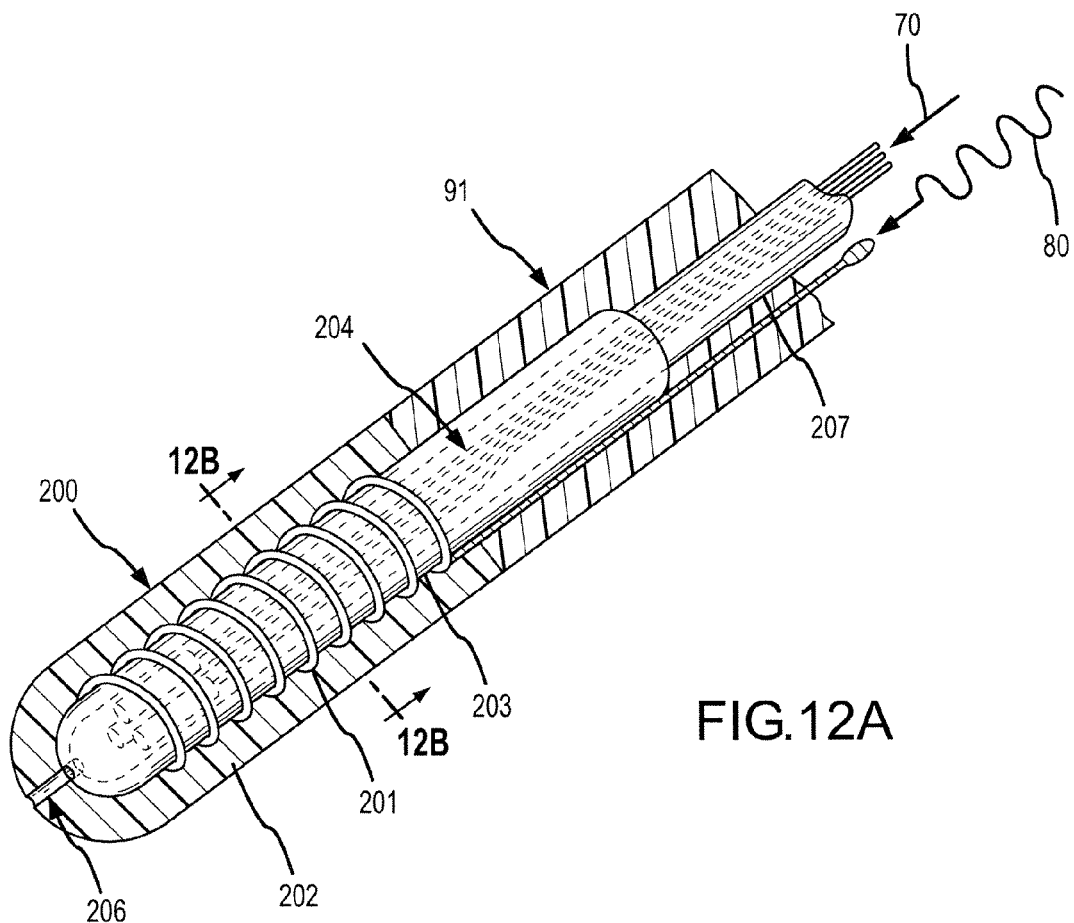
FIGS. 12A and 12B are cross-sectional views of a modified version of the embodiment of FIG. 11A with thermal sensing.
Figure 12B:
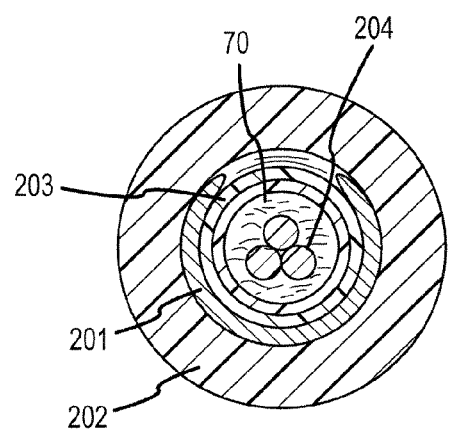

FIGS. 12A and 12B illustrate another preferred embodiment. More particularly, FIGS. 12A and 12B represent a modified version of the embodiment of FIG. 11. Electrode 200 extends from a catheter shaft 91 and is connected to an RF energy source (e.g., RF current source 80). Electrode 200 generally includes: flexible inner conductive coil 201 in the shape of a helix; an outer flexible conductive polymer substrate layer 202; a thermally conductive, electrically insulative flexible tube 203 located partially within the helix of the flexible inner conductive coil 201; a coolant efflux hole 206; and a plurality of thermal sensors 204 located within the thermally conductive, electrically insulative, flexible tube 203 to measure temperatures at various locations therein. Note that a thermally insulative tube 207 is used in at least a portion of the catheter shaft 91 to help reduce the likelihood of cooling fluid 70 being heated to body temperature. In this embodiment, note that thermally conductive, electrically insulative flexible tube 203 also forms the thermally conductive, electrically insulative, flexible shaft which is present in other embodiments.

Figure 13:
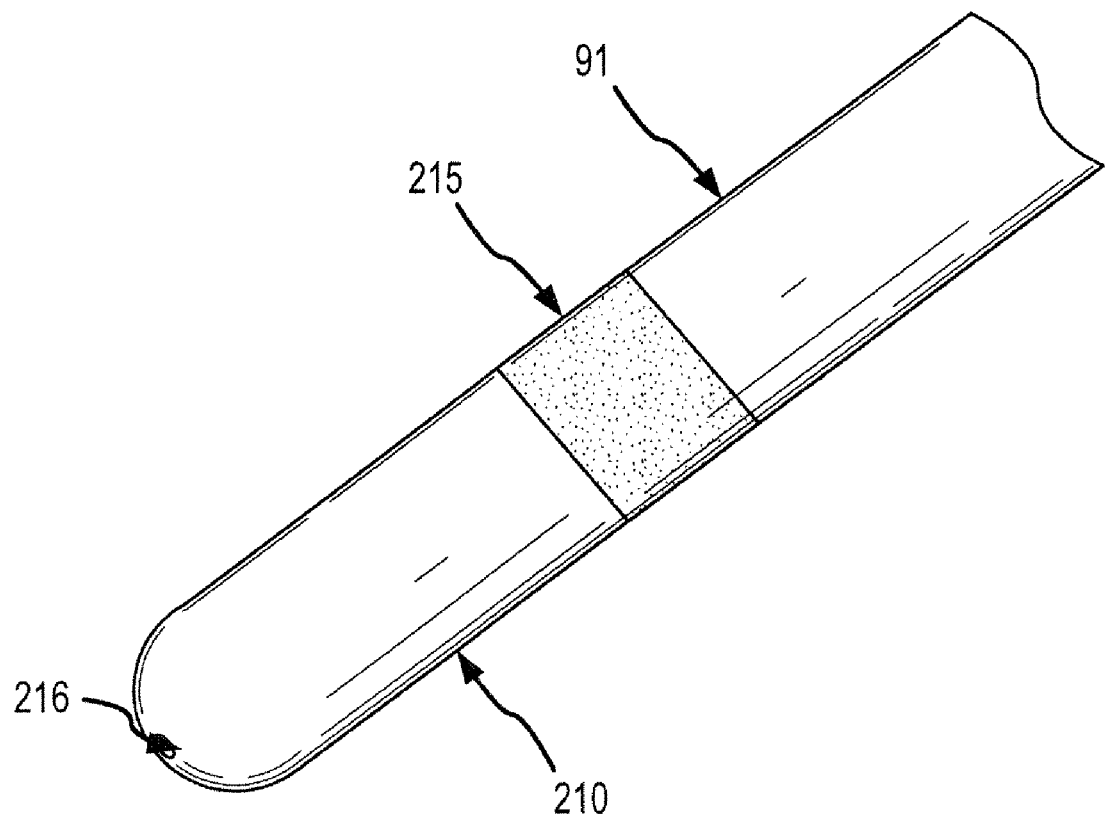
FIG. 13 is a side view of an embodiment that is a modified version of the embodiment of FIG. 10 with a heat sink.

FIG. 13 illustrates yet another preferred embodiment for the invention of the present application. More particularly, FIG. 13 is a modification of the embodiment of FIG. 10. Electrode 210 extends from a catheter shaft 91 and is connected to an RF energy source (not shown). Electrode 210 also includes a heat sink 215 at the proximal end of the electrode and a coolant efflux hole 216 at the distal end of the electrode.

Figure 14A:
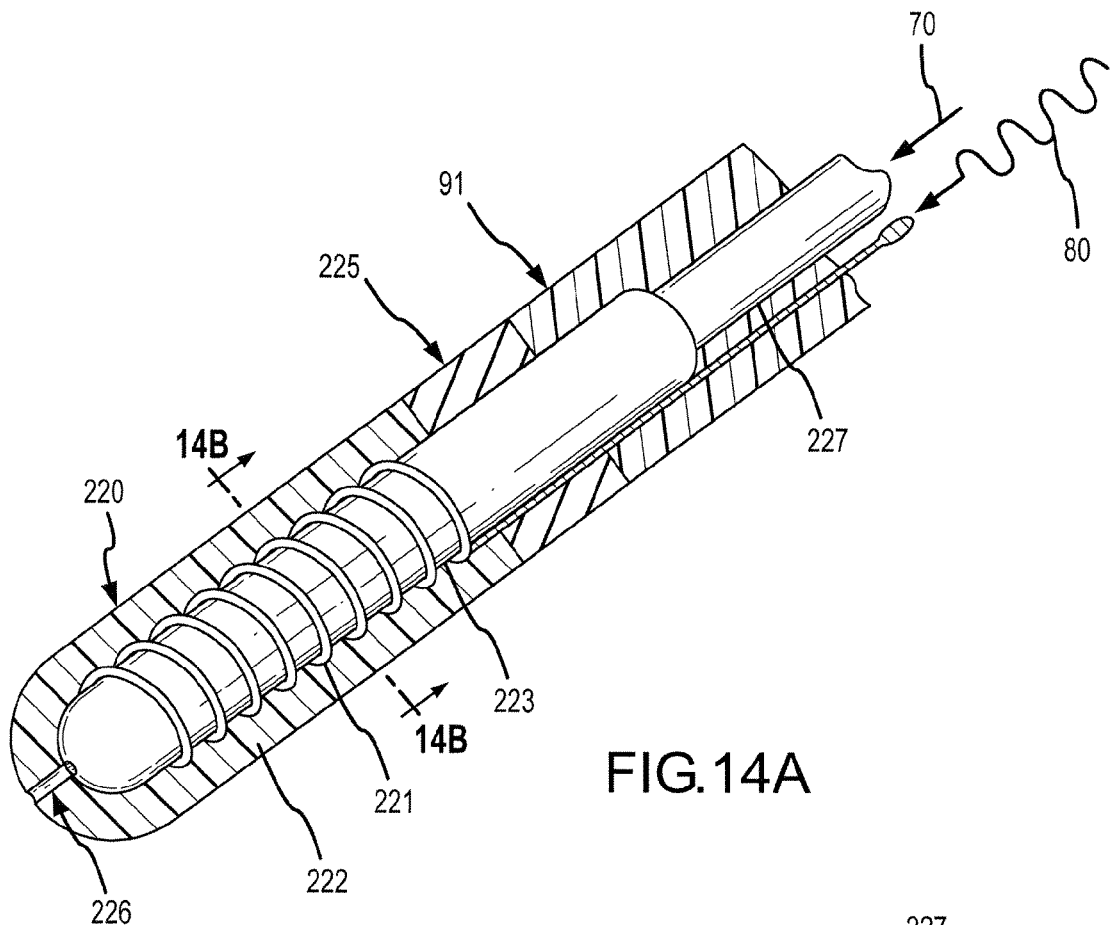
FIGS. 14A and 14B are cross-sectional views of a modification of the embodiment of FIG. 11 with a heat sink.
Figure 14B:
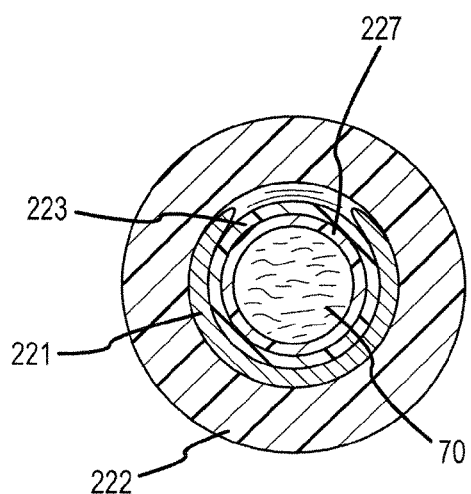

FIGS. 14A and 14B illustrate yet another preferred embodiment. More particularly, FIGS. 14A and 14B represent a modification of the embodiment of FIG. 11. Electrode 220 extends from a catheter shaft 91 and is connected to an RF energy source (e.g., RF current source 80). Electrode 220 generally includes: flexible inner conductive coil 221 in the shape of a helix; an outer flexible conductive polymer substrate layer 222; a thermally conductive, electrically insulative flexible tube 223 located partially within the helix of the flexible inner conductive coil 221; a coolant efflux hole 226; and a heat sink 225 thermally coupled to flexible tube 223. Note that a thermally insulative tube 227 is used in at least a portion of the catheter shaft 91 to help reduce the likelihood of cooling fluid 70 being heated to body temperature. In this embodiment, note that thermally conductive, electrically insulative flexible tube 223 also forms the thermally conductive, electrically insulative, flexible shaft which is present in other embodiments.

Figure 15A:
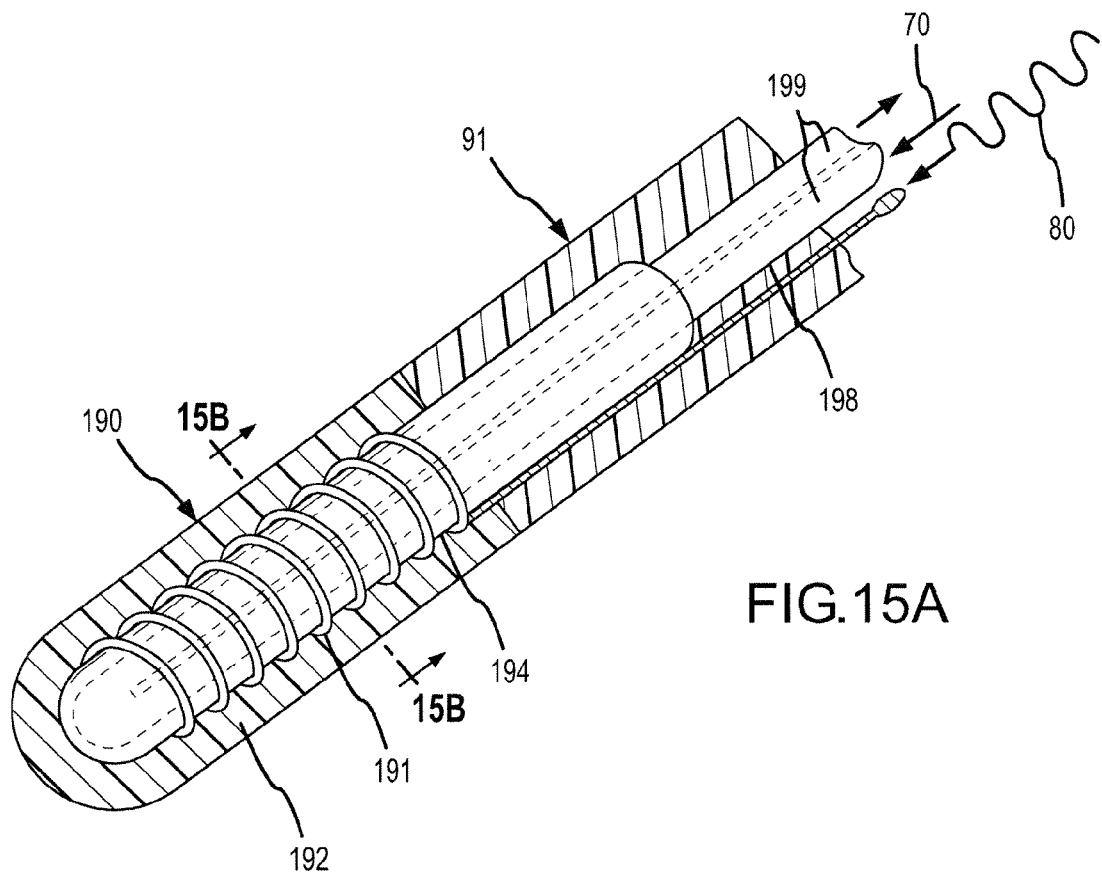
FIGS. 15A and 15B are cross-sectional views of yet another embodiment of the present invention.
Figure 15B:
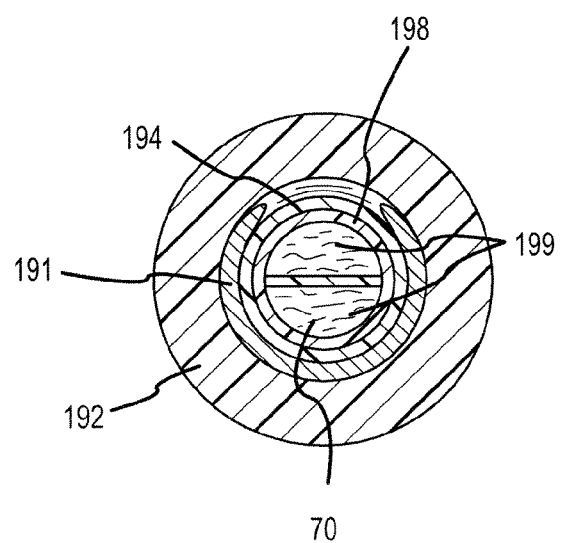

FIGS. 15A and 15B illustrate another preferred embodiment. More particularly, FIGS. 15A and 15B illustrate a preferred embodiment in which a closed loop cooling system has been added. Electrode 190 extends from a catheter shaft 91 and is connected to an RF energy source (e.g., RF current source 80). Electrode 190 generally includes: flexible inner conductive coil 191 in the shape of a helix; an outer flexible conductive polymer substrate layer 192; a thermally conductive flexible shaft 198 located partially within the helix of the flexible inner conductive coil 191; and closed loop cooling passageway 199 located within the flexible shaft 198. Note that a thermally conductive, electrically insulative sleeve 194 may optionally be located between the flexible shaft 198 and inner conductive coil 191. It is contemplated that sleeve 194 may be eliminated, in which case the inner conductive coil 191 may be thermally coupled directly to flexible shaft 198 and closed loop cooling passageway 199. In this embodiment, thermally conductive flexible shaft 198 and closed loop cooling passageway 199 form a closed loop cooling system in which a cooling fluid 70 (e.g., saline) may flow through passageway 199 to cool the distal tip of the catheter during ablation.

In an optional embodiment, any of the electrode designs above may be combined with a processor that monitors the RF current that is being delivered by the RF power source 80. In a preferred embodiment, a computer processor (not shown) will monitor the maximum current being delivered and use this information to help control the ablation process. Using this information, the computer processor (not shown) may decrease or increase the power level of the RF power source. By way of example only, the computer processor (not shown) may be used to limit the total amount of RF energy that is delivered to a certain tissue area. Depending on the nature of the tissue, the power level may be increased to improve lesion creation.

The RF source to be used with the present invention is preferably within the radio frequency range of 200-800 kHz, and more preferably with 250 kHz-550 kHz. The source is preferably capable of delivering up to 150 Watts of electrical power.

The embodiments above may be manufactured in a variety of ways. One such method involves forming an electrode assembly as follows. An electrically insulative shaft may be formed using known electrically insulative materials (which may be thermally conductive or thermally insulative). The shaft is preferably formed of flexible materials. An electrically conductive element for conducting RF energy may be formed on at least a portion of the electrically insulative shaft. In accordance with the teachings above, the conductive element is preferably flexible. A layer of flexible conductive polymer may be formed over at least a portion of the conductive element. In accordance with the teachings above, the electrode assembly may be optionally coated with one or more conductive layers, which are preferably flexible. Preferably, the optional layers are made of a biocompatible, electrically conductive material.

An alternative way to manufacture an electrode assembly of the present invention is as follows. An electrically conductive flexible shaft may be formed using known electrically insulative materials. A layer of flexible conductive polymer may be formed over at least a portion of the conductive shaft. In accordance with the teachings above, the electrode assembly may be optionally coated with one or more flexible conductive layers. Preferably, the optional layers are made of a biocompatible, electrically conductive material.

The electrode assemblies above may also be formed with a fluid lumen and/or one or more fluid efflux holes to permit a cooling fluid to be delivered through the electrode and/or to the tissue during ablation. The assemblies may also be manufactured to include one or more thermal sensors using techniques that are applicable to other known catheter devices.

It is contemplated that each of the embodiments discussed above may optionally be used in connection with one or more electrically-conductive outer coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the device's ability to assess the tissue contact (for example, when measuring electrical characteristics using a reference electrode connected to the target tissue or when using the flexible conductive polymer electrode to measure phase angles). In some cases, the outer covering may be made using a biocompatible material in order to help make the overall assembly biocompatible. Preferably the outer covering is flexible.

It is also contemplated that each of the embodiments discussed above may also incorporate one or more electro-mechanical contact sensors, such as piezoelectric contact sensors, strain gauges, or fiber optic contact sensors. This is described in further detail in U.S. application Ser. No. 11/963,321, filed concurrently herewith and expressly incorporated by reference as though fully set forth herein.

Although multiple embodiments of this invention have been described above with a certain degree of particularity, those skilled in the art could make numerous alterations to the disclosed embodiments without departing from the spirit or scope of this invention. For example, one of skill in the art will appreciate that the various principles and features described above may be employed in numerous combinations and permutations in accordance with the spirit and scope of the present invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode for ablation therapy, the electrode comprising:
    a flexible conductive element for conducting electrical energy; and
    a flexible conductive polymer member that is in electrically conductive contact with the flexible conductive element, wherein the flexible conductive polymer member comprises a pressure sensitive conductive polymer.

2. The electrode according to claim 1, further comprising a catheter shaft coupled to at least one of the flexible conductive element and the flexible conductive polymer member.

3. The electrode according to claim 1, further comprising an ablation energy source coupled to the flexible conductive element such that ablation energy may be delivered via the flexible conductive polymer member.

4. The electrode according to claim 1, wherein the flexible conductive element comprises a helical coil.

5. The electrode according to claim 4, further comprising a flexible electrically insulative member surrounded by at least a portion of the helical coil.

6. The electrode according to claim 5, wherein the flexible electrically insulative member is made of a thermally conductive material.

7. The electrode according to claim 6, further comprising at least one temperature sensor located within the flexible electrically insulative member.

8. The electrode according to claim 5, further comprising a heat sink thermally coupled to at least one of the flexible conductive polymer member and the flexible electrically insulative member.

9. The electrode according to claim 5, wherein the flexible electrically insulative member includes a passageway for coolant fluid to cool the electrode during ablation.

10. The electrode according to claim 9, wherein the passageway includes at least one efflux hole at a distal end of the electrode to permit coolant fluid to flow from the passageway.

11. The electrode according to claim 10, wherein the passageway is defined by a flexible, electrically insulative, and thermally conductive material.

12. The electrode according to claim 10, further comprising:
    a first sensor to measure the temperature of the coolant fluid near the efflux hole; and
    a second sensor to measure the temperature of the coolant fluid at a location other than the efflux hole.

13. The electrode according to claim 12, wherein the second sensor is positioned where the coolant fluid enters the passageway.

14. The electrode according to claim 5, wherein the flexible electrically insulative member includes a passageway for coolant fluid to cool the electrode during ablation, the passageway defining a loop such that coolant fluid travels from a proximal end of the electrode, through a distal end of the electrode, and returns to the proximal end of the electrode via the passageway.

15. The electrode according to claim 1, wherein the flexible conductive element is shaped to form a mesh coating or wrap.

16. The electrode according to claim 15, further comprising a flexible electrically insulative member in mechanical contact with at least a portion of the mesh coating or wrap.

17. The electrode according to claim 16, further comprising a heat sink thermally coupled to at least one of the flexible conductive polymer member and the flexible electrically insulative member.

18. The electrode according to claim 17, wherein the flexible electrically insulative member includes a passageway for coolant fluid to cool the electrode during ablation and an efflux hole at a distal end of the electrode to permit coolant fluid to flow from the passageway.

19. An ablation electrode for ablation therapy, the ablation electrode comprising:
    a flexible electrically insulative member, the member also being thermally conductive;
    a passageway for a coolant fluid to flow through the flexible electrically insulative member to cool the electrode during use;
    a flexible, conductive element for conducting RF energy, the flexible conductive element at least partially covering the flexible electrically insulative member; and
    a layer of flexible conductive polymer that covers at least part of the flexible conductive element, wherein the flexible conductive polymer comprises a pressure sensitive conductive polymer.

20. The ablation electrode according to claim 19, wherein the passageway includes at least one efflux hole in the electrode to permit coolant fluid to flow from the passageway.

21. The ablation electrode according to claim 20, wherein the passageway is defined by an electrically and thermally insulative material that is different from that comprising the electrically insulative member, the electrode further comprising:
    a first sensor to measure the temperature of coolant fluid where it exits one of the at least one efflux hole; and
    a second sensor to measure the temperature of coolant fluid where it enters the passageway.

22. The ablation electrode according to claim 19, wherein the passageway defines a loop such that coolant fluid travels from a proximal end of the electrode, through a distal end of the electrode, and returns to the proximal end of the electrode via the passageway.

23. The ablation electrode according to claim 19, wherein the flexible conductive element is shaped to form a helical coil.

24. The ablation electrode according to claim 19, wherein the flexible conductive element is shaped to form a mesh coating or wrap.

25. The ablation electrode according to claim 19, further comprising a heat sink thermally coupled to at least one of the layer of flexible conductive polymer and the flexible electrically insulative member.

26. A method of manufacturing an electrode for ablation therapy, the method comprising:
    forming an electrically insulative, thermally conductive, flexible shaft;
    forming a flexible, electrically conductive element for conducting RF energy, the conductive element at least partially covering the electrically insulative, thermally conductive, flexible shaft; and
    forming a layer of flexible conductive polymer that covers at least part of the flexible, electrically conductive element, wherein the flexible conductive polymer comprises a pressure sensitive conductive polymer.

27. The method according to claim 26, wherein the step of forming an electrically insulative, thermally conductive, flexible shaft comprises forming an electrically insulative, thermally conductive, flexible shaft, having a passageway through which coolant fluid may flow and having an efflux hole at a distal end of the electrode to permit coolant fluid to flow from the passageway.

28. The method according to claim 26, further comprising forming an electrically insulative, thermally conductive passageway within the electrically insulative, thermally conductive, flexible shaft, the passageway being formed of a material that is different from the material that is used to form the electrically insulative, thermally conductive, flexible shaft.

29. A method of treating tissue, the method comprising:
providing an electrode having a) a flexible conductive element for conducting RF energy and b) a layer of flexible conductive polymer that is in electrical contact with at least a portion of the flexible conductive element, wherein the flexible conductive polymer comprises a pressure sensitive conductive polymer;
coupling an RF energy supply to the flexible conductive element;
positioning the electrode in contact with a tissue specimen to be treated; and
delivering RF energy to the tissue specimen.

30. The method according to claim 29, further comprising:
delivering coolant fluid to an area of the tissue specimen to help control the temperature of the tissue specimen during treatment with RF energy; and
monitoring temperatures at a plurality of locations within the electrode in order to help control the temperature of the tissue specimen during treatment with RF energy.

31. The method according to claim 29, further comprising using a heat sink thermally coupled to the electrode to help control the temperature of the tissue specimen during treatment with RF energy.

32. An electrode for ablation therapy, the electrode comprising:
a conductive element for conducting electrical energy;
a flexible conductive polymer member in electrically conductive contact with the conductive element, wherein the flexible conductive polymer member comprises a pressure sensitive conductive polymer; and
at least one fluid passageway extending through at least a portion of the flexible conductive polymer member and including at least one efflux hole to permit a fluid to exit the flexible conductive polymer member.

33. The electrode according to claim 32, wherein the at least one efflux hole comprises an efflux hole located at a distal end of the electrode.

34. The electrode according to claim 32, wherein the at least one efflux hole comprises a plurality of efflux holes arranged along a length of the electrode.

35. The electrode according to claim 32, further comprising at least one electrically insulative tube extending through the electrode, wherein the at least one fluid passageway is defined by the at least one electrically insulative tube.

36. The electrode according to claim 35, wherein the conductive element is shaped to form a helical coil, and wherein at least a portion of the conductive element is helically coiled about at least a portion of the at least one electrically insulative tube.

37. The electrode according to claim 35, wherein the at least one electrically insulative tube is made of thermally conductive material.

38. The electrode according to claim 32, further comprising a catheter shaft coupled to at least one of the conductive element and the flexible conductive polymer member, wherein the catheter shaft includes at least one fluid passageway that is in fluid communication with the at least one fluid passageway of the electrode.

39. The electrode according to claim 38, wherein the at least one efflux hole comprises at least one efflux hole located at an interface between the ablation electrode and the catheter shaft.

40. The electrode according to claim 32, further comprising at least one temperature sensor located proximate the at least one fluid passageway.

41. The electrode according to claim 40, wherein the at least one temperature sensor is located proximate the at least one efflux hole to measure a temperature of a fluid exiting the at least one efflux hole.

42. The electrode according to claim 40, wherein the at least one temperature sensor is located proximate an inlet to the at least one fluid passageway to measure a temperature of a fluid entering the at least one fluid passageway.

43. The electrode according to claim 32, further comprising an ablation energy source coupled to the conductive element such that ablation energy may be delivered via the flexible conductive polymer member.

44. A method of manufacturing a tissue ablation device, the method comprising:
forming a conductive element;
forming an ablation electrode by covering at least a portion of the conductive element with a flexible conductive polymer material, wherein the flexible conductive polymer material comprises a pressure sensitive conductive polymer; and
forming at least one fluid passageway in the ablation electrode, the at least one fluid passageway including at least one efflux hole to permit a fluid to exit the ablation electrode.

45. The method according to claim 44, wherein the step of forming at least one fluid passageway in the ablation electrode comprises providing at least one electrically insulative tube extending through at least a portion of the flexible conductive polymer material.

46. The method according to claim 45, wherein the step of forming a conductive element comprises forming a conductive element covering at least part of the at least one electrically insulative tube.

47. The method according to claim 44, further comprising:
providing a catheter shaft having a distal end and at least one fluid passageway extending at least partway therethrough; and
coupling the ablation electrode to the distal end of the catheter shaft such that the at least one fluid passageway of the catheter shaft is in fluid communication with the at least one fluid passageway of the ablation electrode.

48. The method according to claim 44, further comprising:
forming an electrically insulative member,
wherein the step of forming a conductive element comprises forming a conductive element covering at least part of the electrically insulative member.

49. A method of treating tissue, the method comprising:
providing an electrode including a flexible conductive element for conducting ablation energy, a flexible conductive polymer material covering at least a portion of the conductive element, wherein the flexible conductive polymer material comprises a pressure sensitive conductive polymer, and a fluid passageway including at least one efflux hole that permits a fluid to exit the electrode;
coupling an ablation energy supply to the conductive element;
positioning the electrode in contact with a tissue specimen to be treated;
delivering ablation energy to the tissue specimen; and
flowing a coolant through the fluid passageway to cool the electrode.

* * * * *